(12) United States Patent
Ho (10) Patent No.: US 8,573,208 B2
(45) Date of Patent: Nov. 5, 2013

(54) EXHAUST ASSEMBLY

(75) Inventor: Peter Chi Fai Ho, Pittsburgh, PA (US)

(73) Assignee: Koninklijke Philips N.V., Eindhoven (NL)

( * ) Notice: Subject to any disclaimer, the term of this patent is extended or adjusted under 35 U.S.C. 154(b) by 253 days.

(21) Appl. No.: 12/991,449

(22) PCT Filed: May 1, 2009

(86) PCT No.: PCT/IB2009/051790
§ 371 (c)(1),
(2), (4) Date: Nov. 8, 2010

(87) PCT Pub. No.: WO2009/136333
PCT Pub. Date: Nov. 12, 2009

(65) Prior Publication Data
US 2011/0056495 A1   Mar. 10, 2011

Related U.S. Application Data

(60) Provisional application No. 61/051,093, filed on May 7, 2008.

(51) Int. Cl.
*A62B 7/00* (2006.01)
*A62B 7/04* (2006.01)
*A62B 18/10* (2006.01)
*A61M 16/00* (2006.01)
*F16K 31/26* (2006.01)

(52) U.S. Cl.
USPC ............ 128/205.24; 128/201.28; 128/204.18; 128/204.26

(58) Field of Classification Search
USPC ............ 128/200.29, 201.27, 201.28, 204.18, 128/204.26, 204.27, 204.29, 205.24, 128/205.25, 206.21, 206.28, 207.13, 128/207.21, 911, 912, 207.12; 604/43, 45; 251/61, 61.1; 137/505.26, 505.36, 908, 137/115.16, 115.27
See application file for complete search history.

(56) References Cited

U.S. PATENT DOCUMENTS 3,429,342 A   2/1969   Garrett
3,460,558 A   8/1969   Johannisson
3,467,136 A   9/1969   Masson
(Continued)

FOREIGN PATENT DOCUMENTS

DE   2748055 A1   5/1978
SU   1015344 A    4/1983
SU   1015344 A1   4/1983
WO   WO2004022147 A1   3/2004

*Primary Examiner* — Jackie Ho
*Assistant Examiner* — Mark K Han
(74) *Attorney, Agent, or Firm* — Michael W. Haas (57) ABSTRACT

An exhaust assembly (1) adapted for use in a respiratory gas delivery system comprises an exhaust vent, an exhaust gas flow passage, a primary gas flow passage, and a moveable member. The exhaust gas flow passage communicated a flow of exhaust gas from a first end of the exhaust assembly to the exhaust vent. The exhaust vent communicates the exhaust gas from the exhaust gas flow passage to ambient atmosphere. The primary gas flow passage communicates a flow of supply gas from a second end of the exhaust assembly to the first end of the exhaust assembly. The moveable member defines at least a portion of the exhaust gas flow passage and the primary gas flow passage, is operable to isolate the flow of exhaust gas from the flow of supply gas, and is responsive to a pressure differential between the flow of supply gas and the flow of exhaust gas.

15 Claims, 5 Drawing Sheets

(56) References Cited

U.S. PATENT DOCUMENTS

| | | |
|---|---|---|
| 3,473,571 A | 10/1969 | Dugay |
| 3,474,831 A | 10/1969 | Noakes |
| 3,592,237 A | 7/1971 | Borschers |
| 3,770,104 A | 11/1973 | Reimers |
| 3,948,289 A | 4/1976 | Stephens |
| 3,951,379 A | 4/1976 | Cornelius |
| 4,182,371 A | 1/1980 | Moore |
| 4,234,013 A | 11/1980 | Rikuta |
| 4,239,038 A * | 12/1980 | Holmes .................... 128/205.13 |
| 4,280,527 A | 7/1981 | Pease |
| 4,351,510 A | 9/1982 | Welker |
| 4,354,516 A | 10/1982 | Newell |
| 4,428,397 A | 1/1984 | Bron |
| 5,002,050 A | 3/1991 | McGinnis |
| 5,148,802 A | 9/1992 | Sanders |
| 5,438,981 A | 8/1995 | Starr |
| 5,685,296 A | 11/1997 | Zdrojkowski |
| 5,937,855 A | 8/1999 | Zdrojkowski |
| 6,513,519 B2 * | 2/2003 | Gallem .................... 128/200.14 |
| 6,584,977 B1 | 7/2003 | Serowski |
| 2004/0094157 A1 * | 5/2004 | Dantanarayana et al. .................... 128/206.21 |
| 2005/0166923 A1 | 8/2005 | Hollis |
| 2005/0172969 A1 * | 8/2005 | Ging et al. .................... 128/206.24 |

* cited by examiner

EXHAUST ASSEMBLY

BACKGROUND OF THE INVENTION

1. Field of the Invention

The present invention pertains to an apparatus employed in the delivery of a flow of breathing gas to the airway of a patient, and, more particularly, to an exhaust assembly adapted to provide a controlled flow of exhaust gas over a range of supply pressures.

2. Description of the Related Art

A ventilation circuit, also commonly referred as a breathing circuit or a patient circuit, may be employed to supply a continuous flow of breathing gas to the airway of a spontaneously breathing patient. The ventilation circuit may include an exhaust assembly which provides an exhaust flow path for air exhaled by the patient. During the exhalation phase of the patient's breathing, exhalation gas backflows into the ventilation circuit and, unless exhausted from the circuit, is re-breathed by the patient during the next inhalation phase. Re-breathing of exhaled gas is undesirable because the exhalation flow contains carbon dioxide ($CO_2$). Reliable and thorough exhaustion or purging of exhalation gas from the ventilation circuit is, thus, an important feature of such ventilation circuits. This purging becomes a more difficult problem the further the exhalation valve is located from the patient interface due to the amount of residual exhaled gas in the intervening ventilation circuit dead space.

Conventional exhalation assemblies provide varying fluid flow at varying fluid pressures. However, the naturally occurring relationship of fluid flow rate to pressure (flow is proportional to the square root of pressure) may be unacceptable in a ventilation circuit for a number of reasons. In medical ventilators used to assist patient breathing and in similar devices used to supply breathing gas to a spontaneously breathing patient, for example, it has been common practice to include a fixed size leak, especially in single limb patient circuits. The size of the leak is selected such that the exhaust gas is flushed out of the patient circuit before the exhaled gas can be re-breathed by the patient with the next inhalation. The fixed sized, i.e., fixed geometry or fixed orifice, leak may be provided by an exhalation valve. However, an exhalation valve with a flow characteristic that varies naturally with pressure variations in the patient circuit may not be suitable as a patient circuit exhaust valve.

Additionally, some pressure support systems are adapted to supply bi-level pressure support in which the pressure of the air supplied to the patient during exhalation is lower than the pressure of the air supplied to the patient during inhalation. With many conventional exhalation valves, the size of the fixed leak needed to flush exhaled gas from the circuit under the relatively lower pressure of exhalation is very large. However, the flow rate through such a fixed leak at the higher inhalation pressure results in enormous waste of supply gas during inhalation. Such conditions may require a larger capacity pressure generator, commonly a blower, for example, than would otherwise be required. This too is wasteful in that the result is unnecessary added cost for the apparatus and increased energy consumption to operate it.

It is, therefore, preferable that the flow rate of the leak provided to flush exhaled gas from such a ventilation circuit does not change appreciably within the range of pressures applied in the circuit. In this sense, a fixed leak is more desirable than one that provides a fixed flow rate, than one characterized by a flow path cross-sectional area of fixed size.

Among the prior art of valves purporting to regulate flow by means of pressure actuated regulators are those disclosed in U.S. Pat. Nos. 3,467,136, 3,474,831, 3,592,237, 3,948,289 and 3,951,379. Other flow regulating valves are disclosed in U.S. Pat. Nos. 3,429,342, 3,473,571, 3,770,104, 4,182,371, 4,234,013, 4,280,527, 4,351,510 and 4,354,516. U.S. Pat. No. 4,428,397, apparently related German Patent no. DE 27 48 055 A1, and Russian Patent abstract SU 1015344A disclose a valve for controlling the rate of flow of fluid therethrough. In addition, U.S. Pat. No. 5,002,050 discloses a medical gas flow control valve and U.S. Pat. No. 5,438,981 discloses an automatic safety valve and diffuser for a nasal and/or oral gas delivery mask.

U.S. Pat. Nos. 5,685,296 and 5,937,855 disclose a flow regulating valve that exhausts gas from a ventilation circuit at a constant flow rate despite varying pressure in the ventilation circuit. However, as noted above, it may be further desirable to locate the exhaust valve at the mask, for example, so that the amount of ventilation circuit dead space is minimized and so that the need to provide a relatively bulky exhaust structure on the ventilation circuit is eliminated. In treating obstructive sleep apnea OSA, for example, a positive pressure therapy is provided to the patient while he or she sleeps. Therefore, it is preferable for the patient circuit to be flexible and readily movable during the pressure support treatment. This goal may be frustrated by providing the exhaust valve on the patient circuit. In the hospital setting, it is also preferable to minimize the entanglements on the patient circuit to keep as clear a working area as possible for the doctors and nurses.

Accordingly, a need exists for an apparatus and method for providing improved comfort for a patient receiving a flow of breathing gas which overcomes these and other problems associated with known systems.

SUMMARY OF THE INVENTION

In accordance with an aspect of the present invention, an exhaust assembly adapted for use in a respiratory gas delivery system comprises an exhaust vent, an exhaust gas flow passage, a primary gas flow passage, and a moveable member. The exhaust gas flow passage is structured to communicate a flow of exhaust gas from a first end of the exhaust assembly to the exhaust vent. The exhaust vent is structured to communicate the flow of exhaust gas from the exhaust gas flow passage to ambient atmosphere. The primary gas flow passage is structured to communicate a flow of supply gas from a second end of the exhaust assembly to the first end of the exhaust assembly. The moveable member defines at least a portion of the exhaust gas flow passage and the primary gas flow passage, is operable to isolate the flow of exhaust gas in the exhaust gas flow passage from the flow of supply gas in the primary gas flow passage, and is responsive to a pressure differential between the flow of supply gas in the primary gas flow passage and the flow of exhaust gas in the exhaust gas flow passage.

According to another aspect of the present invention, an elbow assembly for a respiratory mask comprises an elbow, wherein the elbow comprises an inlet adapted to couple with a flow generating device and an outlet adapted to couple with a patient interface device. The elbow further defines a primary gas flow passage adapted to communicate a flow of breathing gas from such flow generator to such patient interface device, an exhaust vent, an exhaust gas flow passage adapted to communicate a flow of exhaust gas from such patient interface device to the exhaust vent, wherein the exhaust vent is adapted to communicate the flow of exhaust gas from the exhaust gas flow passage to atmosphere, and a partition disposed in the elbow and structured to isolate the flow of breathing gas within the primary gas flow passage from the flow of exhaust gas in the exhaust gas flow passage, the partition including a moveable member structured to be responsive to a pressure differential between the flow of breathing gas in the primary gas flow passage and the flow of exhaust gas in the exhaust gas flow passage.

According to another aspect of the present invention, a patient circuit comprises an exhaust assembly, wherein the exhaust assembly comprises a first end and a second end. The exhaust assembly further defines a primary gas flow passage defined between the first end and the second end, an exhaust gas flow passage, an exhaust vent structured to fluidly connect the exhaust gas flow passage to ambient atmosphere through a wall of the exhaust assembly, wherein the exhaust gas flow passage extends from the first end to the exhaust vent, and a partition disposed in the exhaust assembly and structured to isolate the primary gas flow passage from the exhaust gas flow passage, the partition including a moveable member structured to be responsive to a pressure differential between the primary gas flow passage and the exhaust passage.

According to another aspect of the present invention, a patient circuit comprises an exhaust assembly, wherein the exhaust assembly comprises a first end and a second end. The exhaust assembly further defines a primary gas flow passage defined therein from the first end to the second end and an exhaust gas flow passage defined therein, an exhaust vent structured to fluidly connect the exhaust gas flow passage to ambient atmosphere through a wall of the exhaust assembly, wherein the exhaust gas flow passage extends from the first end to the exhaust vent, a rigid wall disposed in the exhaust assembly defined between the primary gas flow passage and the exhaust gas flow passage so as to isolate the primary gas passage from the exhaust gas flow passage, and a flow regulating member associated with the exhaust gas flow passage to control a rate of flow of exhaust gas passing to atmosphere through the exhaust gas flow passage by moving the flow regulating member into the exhaust gas flow path, wherein a degree of movement of the flow regulating member into the exhaust gas flow path increases as a pressure in the primary gas flow passage increases relative to a pressure in the exhaust gas flow passage.

According to another aspect of the present invention, a patient circuit comprises an exhaust assembly wherein the exhaust assembly comprises a first end and a second end. The exhaust assembly further defines a primary gas flow passage defined therein from the first end to the second end, and an exhaust gas flow passage defined therein, an exhaust vent structured to fluidly connect the exhaust gas flow passage to ambient atmosphere through a wall of the exhaust assembly, wherein the exhaust gas flow passage extends from the first end to the exhaust vent, a rigid wall disposed in the exhaust assembly defined between the primary gas flow passage and the exhaust gas flow passage so as to isolate the primary gas passage from the exhaust gas flow passage, and a flow regulating assembly operatively associated with the primary gas flow passage and the exhaust gas flow passage, wherein the flow regulating assembly is configured and arranged so as to pass a substantially continuous flow of gas from the exhaust gas flow passage to ambient atmosphere at a substantially constant flow rate irrespective of variation of pressure in the primary gas flow passage.

According to another aspect of the invention, a method for providing a regimen of respiratory therapy comprises delivering a flow of breathing gas to a patient via a patient circuit having an exhaust assembly configured and arranged so as to pass a substantially continuous flow of gas from the patient circuit to ambient atmosphere at a substantially constant flow rate irrespective of variation of pressure in the flow of breathing gas. The exhaust assembly comprises a first end and a second end, and further defines a primary gas flow passage defined therein from the first end to the second end, and an exhaust gas flow passage defined therein, an exhaust vent structured to fluidly connect the exhaust gas flow passage to ambient atmosphere through a wall of the exhaust assembly, wherein the exhaust gas flow passage extends from the first end to the exhaust vent, a rigid wall disposed in the exhaust assembly defined between the primary gas flow passage and the exhaust gas flow passage so as to isolate the primary gas passage from the exhaust gas flow passage, and a flow regulating assembly operatively associated with the primary gas flow passage and the exhaust gas flow passage.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE EXEMPLARY EMBODIMENTS

Directional phrases used herein, such as, for example, left, right, clockwise, counterclockwise, top, bottom, up, down, and derivatives thereof, relate to the orientation of the elements shown in the drawings and are not limiting upon the claims unless expressly recited therein.

As employed herein, the statement that two or more parts are "connected", "coupled", or "attached" shall mean that the parts are joined or operate together either directly or joined or operate together through one or more intermediate parts. As employed herein, the term "number" shall mean one or more than one and the singular form of "a", "an", and "the" include plural referents unless the context clearly indicates otherwise.

Figure 1:
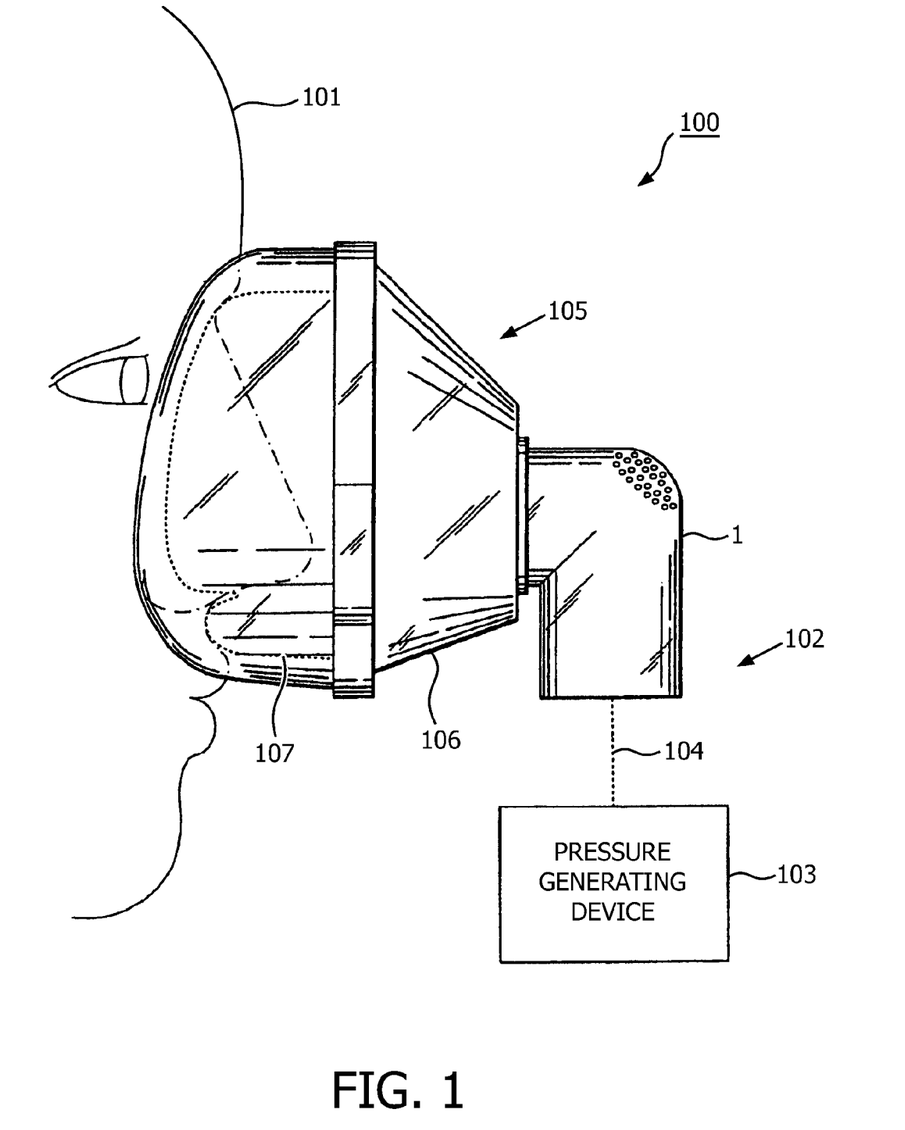
FIG. 1 is a schematic view of a system adapted for communicating a flow of breathing gas to an airway of patient according to an embodiment of the present invention.

A respiratory gas delivery system 100 adapted to provide a regimen of respiratory therapy to a patient according to one embodiment is generally shown in FIG. 1. System 100 includes a pressure generating device 103, a patient circuit 102, and a patient interface device 105. Pressure generating device 103 is structured to generate a flow of supply gas (also referred to herein as "breathing gas") and may include, without limitation, ventilators, continuous pressure support devices (such as a continuous positive airway pressure device, or CPAP device), variable pressure devices (e.g., BiPAP®, Bi-Flex®, or C-Flex™ devices manufactured and distributed by Respironics, Inc. of Murrysville, Pa.), auto-titration pressure support systems, and even tanks of pressurized gas. As the prior art is replete with descriptions of the various types of pressure generating devices, no further description of these items is necessary for present purposes.

Patient circuit 102 is structured to communicate the flow of breathing gas from pressure generating device 103 to patient interface device 105. In the current embodiment, patient circuit 102 includes a conduit 104 and an exhaust assembly 1 that are, as will be discussed in more detail herein, adapted to control a flow of exhaust gas discharged from system 100 over a range of supply pressures. Although illustrated as separate components, it is contemplated that conduit 104 and exhaust assembly 1 can be combined into a single component while remaining within the scope of the present invention.

Patient interface 105 is typically a nasal or nasal/oral mask structured to be placed on and/or over the face of a patient 101. Any type of patient interface device 105, however, which facilitates the delivery of the flow of breathing gas communicated from pressure generating device 103 to the airway of patient 101 may be used while remaining within the scope of the present invention. In the embodiment illustrated in FIG. 1, patient interface 105 includes a rigid shell 106 and a cushion 107. By conforming to the face of patient 101, cushion 107 is adapted to create an airtight seal between patient interface 105 and the face of patient 101. Accordingly, the flow of breathing gas from pressure generating device 103 is communicated via patient circuit 102, through shell 106, to the airway of patient 101. As shown in FIG. 1, shell 106 is adapted to directly couple with exhaust assembly 1; other arrangements, however, are contemplated.

FIGS. 2-5 provide several different views of an exhaust assembly 1, according to one embodiment of the present invention. In this embodiment, exhaust assembly 1 is a 90° elbow that couples conduit 104 to patient interface device 105. It is to be understood, however, that the present invention contemplates the use of a variety of configurations for exhaust assembly 1. For example, an elbow of less than 90° may be used while remaining within the scope of the present invention.

Figure 2:
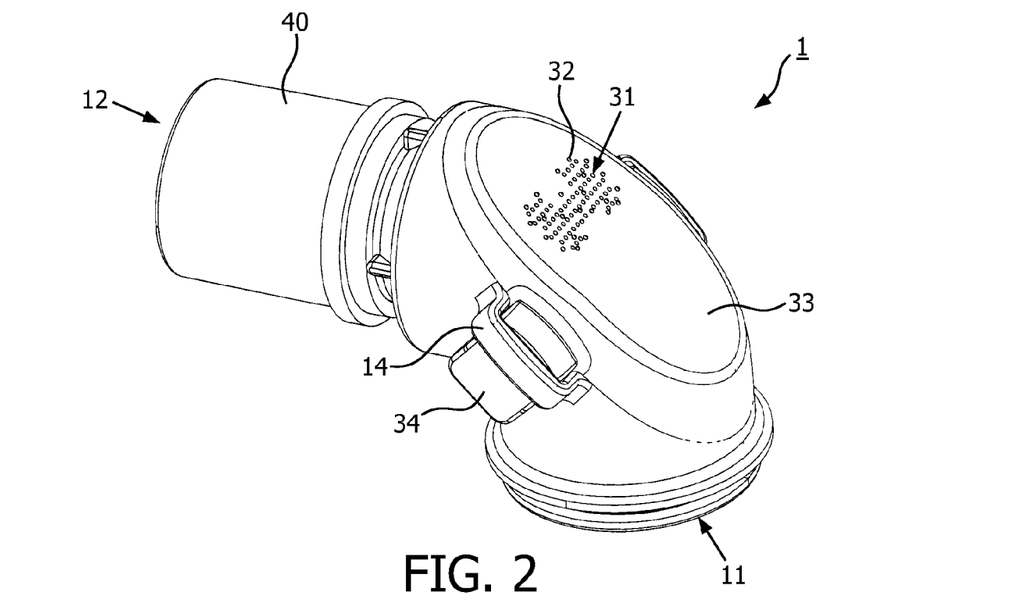
FIG. 2 is a perspective view of an exhaust assembly according to one embodiment of the present invention.
Figure 3:
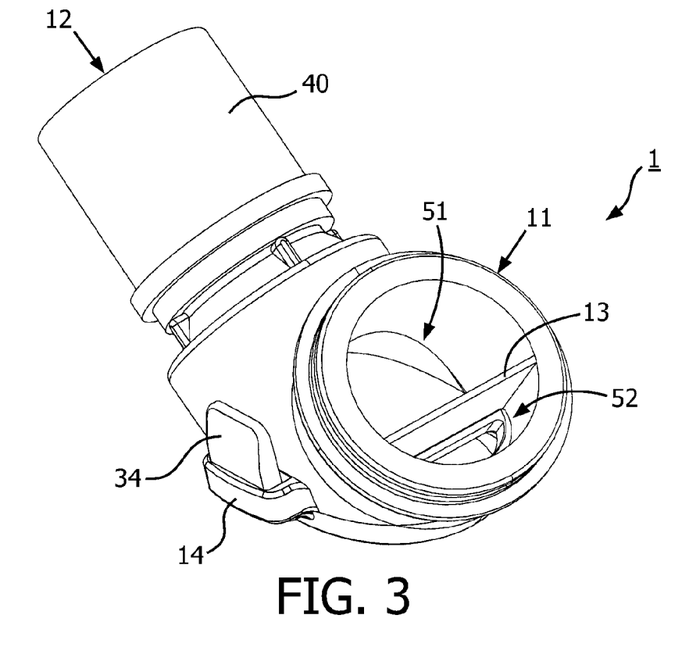
FIG. 3 is a perspective view, from a first end, of the exhaust assembly shown in FIG. 2.

Referring to a FIG. 2, exhaust assembly 1 includes an outlet (i.e., first end) 11, which is adapted to rotatably couple with a patient interface device (for example, patient interface device 105 as shown in FIG. 1), an inlet (i.e., second end) 12, which is adapted to couple with a flow generating device (for example, to flow generating device 103 as shown in FIG. 1), and an exhaust vent 31 which is adapted to communicate a flow of exhaust gas from the interior of exhaust assembly 1 to atmosphere.

Figure 4:
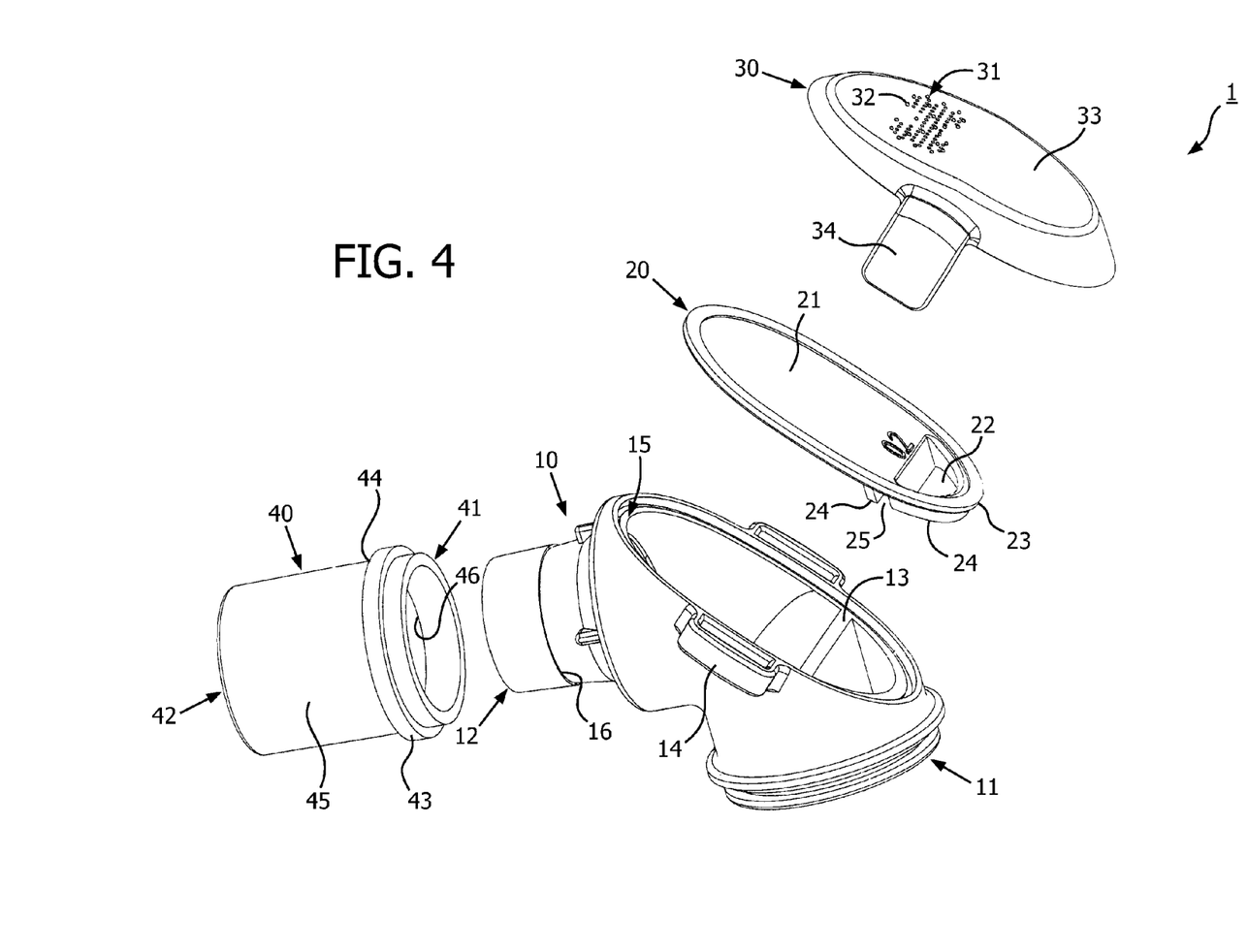
FIG. 4 is an exploded view of the exhaust assembly shown in FIG. 2.

Referring now to FIG. 4, exhaust assembly 1 generally includes a base portion 10, a moveable member 20, an exhaust portion 30, and a coupler 40. It should be apparent to one skilled in the art that the functions and/or structures of one or more of the various components may be combined and/or modified without departing from the scope of the present invention.

A first end 41 of coupler 40 is adapted to rotatably couple to inlet 12 of base portion 10. Coupler 40, for example, is structured to slide over inlet 12 until an edge 46 of coupler 40 engages an edge 16 of base portion 10 (see FIG. 5). Engagement of edge 46 with edge 16 prevents coupler 40 from disengaging from base portion 10 while still allowing coupler 40 to freely rotate relative to base portion 10. A second end 42 of coupler 40 is adapted to connect with a supply conduit. For example, coupler 40 is adapted such that an end of conduit 104 (as shown in FIG. 1) slides over the outer surface 45 of coupler 40 and abuts stop 44 of ring 43. Friction between conduit 104 and outer surface 45 prevents conduit 104 and coupler 40 from disengaging. Such friction fits are well known in the art; thus, no further description of such a fit is necessary for present purposes. It is contemplated, however, that other types of connections may be utilized to connect coupler 40 to conduit 104.

In the current embodiment, base portion 10 includes a rigid member 13 which in conjunction with moveable member 20 form a partition that, as will be discussed in more detail below, divides the interior of base portion 10 into two flow paths. Rigid member 13 generally extends from outlet 11 to the bottom portion of recess 15. Base portion 10 also includes a number of retention slots 14, here located on each side of base portion 10.

Moveable member 20 includes an aperture 22, an outer rim 23, and protrusions 24. Protrusions 24 define a slot 25. Moveable member 20 is adapted such that when exhaust assembly 1 is assembled, outer rim 23 rests within recess 15 of base portion 10 and rigid member 13 is received within slot 25.

Exhaust portion 30 includes vent 31 which generally is comprised of a number of orifices, or holes, 32. Orifices 32 allow a flow of gas to be communicated through a wall 33 of exhaust portion 30. A number of tabs 34 are disposed about exhaust portion 30. Tabs 34 are structured to be inserted into and engage retention slots 14 located on each side of base portion 10. Tabs 34 and retention slots 14 are structured to join base portion 10 to exhaust portion 30, while retaining moveable member 20 therebetween. Other means for joining base portion 10 with exhaust portion 30 are also contemplated.

Figure 5:
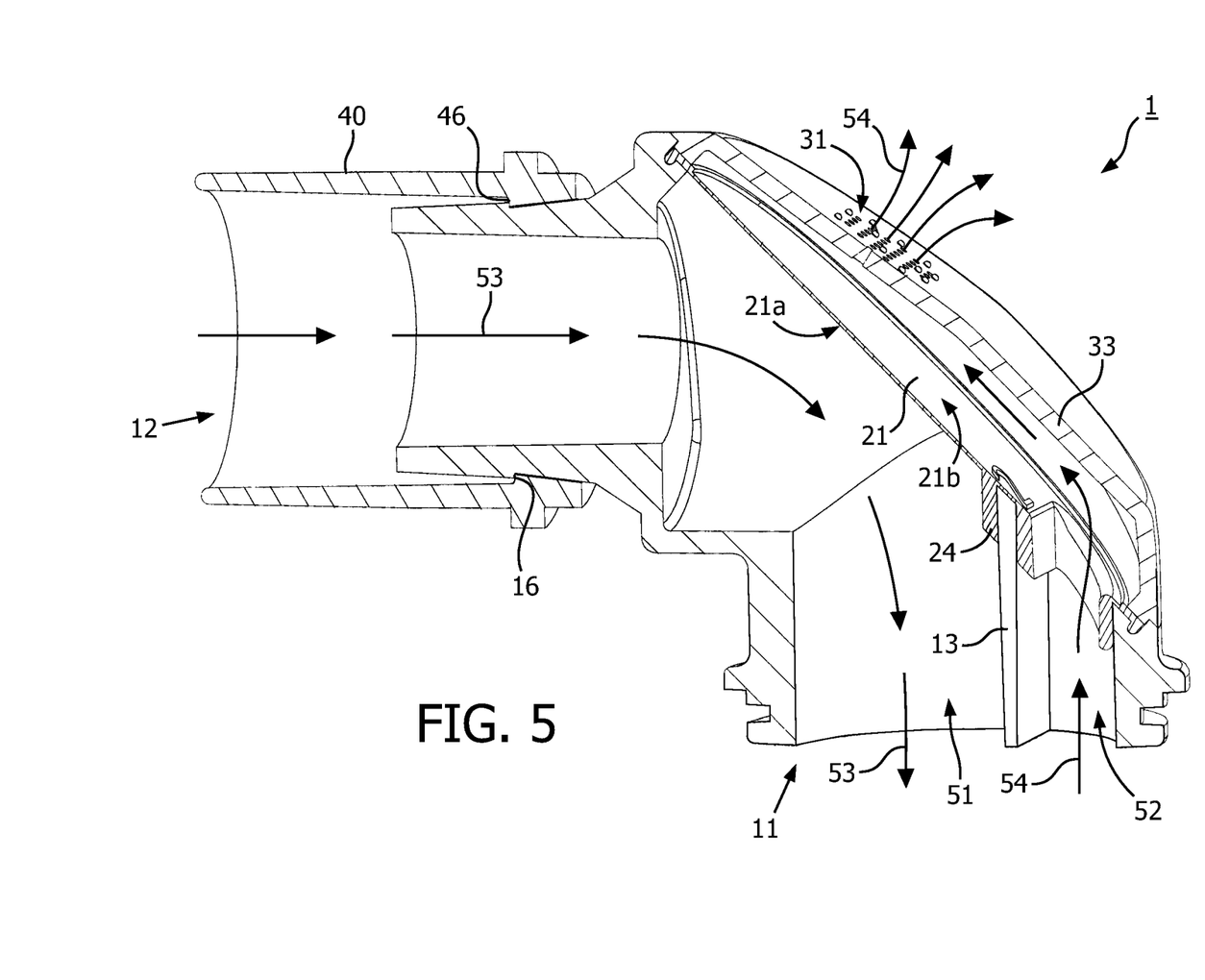
FIG. 5 is a cross-sectional view of the exhaust assembly shown in FIG. 2.

As best seen in FIG. 5, rigid member 13 and movable member 20 help define a primary gas flow passage 51 (which extends from inlet 12 to outlet 11) and an exhaust gas flow path 52 (which extends from outlet 11 to exhaust vent 31) within exhaust assembly 1. More specifically, rigid member 13 and moveable member 20, together with the wall of base portion 10 and wall 33 of exhaust portion 30, define an exhaust gas flow passage 52 between outlet 11 and exhaust vent 31. Rigid member 13 and moveable member 20, together with the wall of base portion 10, also define primary gas flow passage 51 between outlet 11 and inlet 12. Rigid member 13 and flexible surface 21 of moveable member 20 keep any flow of gas present within primary gas flow passage 51 separated from any flow of gas present within exhaust gas flow passage 52. Although the partition in the current embodiment includes a rigid member 13 and a moveable member 20, other arrangements are contemplated. For example and without limitation, it is contemplated that the partition can be constructed of only a moveable member 20.

Exhaust gas flow passage 52 is structured to communicate a flow of exhaust gas (generally indicated by arrows 54) from outlet 11 to exhaust vent 31. Exhaust vent 31 is structured to communicate the flow of exhaust gas 54 from exhaust gas flow passage 52 to ambient atmosphere. Primary gas flow passage 51 is structured to communicate a flow of supply gas (generally indicated by arrows 52) from inlet 12 to outlet 11. Moveable member 20 defines at least a portion of the exhaust gas flow passage 52 and the primary gas flow passage 51, is operable to isolate the flow of exhaust gas 54 in the exhaust gas flow passage 52 from the flow of supply gas 53 in the primary gas flow passage 51, and is responsive to a pressure differential between the flow of supply gas 53 in the primary gas flow passage 51 and the flow of exhaust gas 54 in the exhaust gas flow passage 52.

In operation, moveable member 20 functions as a flow regulator by increasing the resistance that the flow of exhaust gas 54 encounters in passing to atmosphere through the exhaust gas flow passage 52. In the current embodiment, moveable member 20 moves into and effectively alters the cross-sectional area of exhaust gas flow passage 52 in response to the difference between the pressure in the primary gas flow passage 51 and the pressure in the exhaust gas flow passage 52. The degree of movement of moveable member 20 into exhaust gas flow passage 52 increases as a pressure in the primary gas flow passage 51 increases relative to a pressure in exhaust gas flow passage 52. For example as seen in FIG. 5, the greater the pressure exerted by the flow of supply gas 53 on side 21a of flexible membrane 21 relative to the pressure exerted by the flow of exhaust gas 54 on side 21b of flexible membrane 21, the more moveable member 20 moves into exhaust gas flow passage 52. As less pressure is exerted by the flow of supply gas 53 on side 21a relative to the pressure exerted by the flow of exhaust gas 54 on side 21b, the more moveable member 20 returns to its at-rest state and the less exhaust gas flow passage 52 is blocked.

In the current embodiment, the rate of flow of exhaust gas 54 is controlled by at least one of the size of aperture 22 (which admits the flow of exhaust gas 54 into the exhaust gas flow passage 52), the flexibility of membrane 21, and the number, size, and/or location of orifices 32. Other design features and/or structures may also be used to control the rate of flow of exhaust gas 54. For example, the spacing between wall 33 and membrane 21 may be altered to change the cross-sectional area of the exhaust gas flow passage 52, thus changing the rate of flow of exhaust gas 54. As yet another example, elastic membrane 21 may be replaced by, or employed in conjunction with, a piston or other structure which alters the area of the exhaust gas flow passage 52 in response to the difference in pressure between in the primary gas flow passage 51 and the pressure in the exhaust gas flow passage 52. The amount that the piston moves in response to this pressure differential can be predetermined, for example, by selection of the piston's set spring constant.

Moveable member 20 is configured and arranged so as to control the passage of a substantially continuous flow of exhaust gas 54 from the exhaust gas flow passage 52 to ambient atmosphere at a substantially constant flow rate irrespective of variation of pressure in the primary gas flow passage 51. From the above description, it can be appreciated that the pressure differential across moveable member 20 created by the difference between the pressure within primary gas flow passage 51 and the pressure within exhaust gas flow passage 52 will tend to force moveable membrane 20 into exhaust gas flow passage 52, thereby diminishing the effective cross-sectional area of the exhaust gas flow passage 52 by a pre-determinable amount and hence regulating the flow of exhaust gas 54. The amount by which the effective cross-sectional area of exhaust gas flow passage 52 is diminished will depend on the magnitude of the pressure differential to which moveable member 20 is subjected. When the pressure differential increases, moveable member 20 is deformed into exhaust gas flow passage 52 by a further increment, thereby decreasing the cross-sectional area of the exhaust gas flow passage 52, and when the differential pressure decreases, moveable member 20 recoils, thus, increasing the cross-sectional area of exhaust gas flow passage 52.

The geometry, dimensions, and material properties (such as, the hardness for example, in durometer) of moveable member 20, aperture 22, exhaust gas flow passage 52, and/or primary gas flow passage 51, as well as the geometry, dimensions, and number of orifices 32 in exhaust vent 31, may be selected to provide the desired control over the flow rate of the exhaust gas flow passage 52 over a range of pressures provided by a pressure generating device. For example, the present invention contemplates that the cross-sectional area of exhaust gas flow passage 52 diminishes and increases such that, in response to increasing and decreasing pressure differentials, respectively, the rate of flow of the exhaust gas 54 remains essentially constant over a range of expected ventilation circuit pressures. The specific configurations shown in the figures are provided for illustration purposes and are not intended to be the only possible configuration for accomplishing this function.

In the embodiment illustrated in FIGS. 2-5, moveable member 20 is a resiliently deformable, elastic membrane (such as, and without limitation, silicone rubber). It is contemplated; however, that moveable member 20 can encompass other structures (such as and without limitation, a piston and spring combination) which are responsive to the pressure differential between the primary gas flow passage 51 and the exhaust gas flow passage 52.

Figure 6:
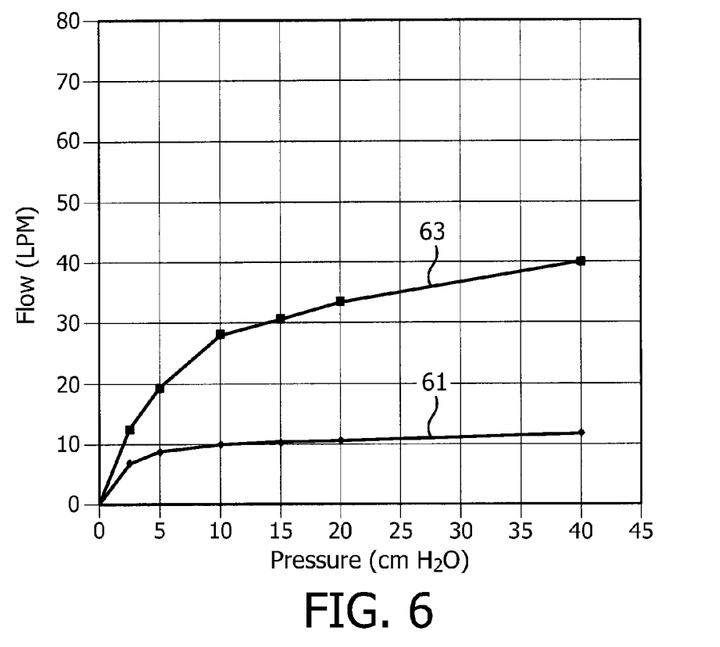
FIG. 6 is a pressure flow curve illustrating the effect of changing the durometer of a moveable membrane within the exhaust assembly.

It is further contemplated that the flow characteristics of the exhaust assembly 1 may be easily tailored to a specific flow rate, for example, by using different moveable membranes 20. FIG. 6, for example, illustrates the flow characteristics for different moveable member 20; each with an elastic membrane 21 having the same thickness (i.e., 0.3 mm or 0.012 inches), but having differing durometer (i.e., hardness). Generally, the greater the durometer of the membrane, the less elastic it becomes. The line identified by numeral 61 in FIG. 6, for instance, illustrates that a membrane with a durometer of 10 has a flow plateau level of approximately 10-12 LPM over a pressure range of 20 to 40 cmH$_2$0; whereas the line identified by numeral 63 illustrates that a membrane with a durometer of 20 has a flow plateau level of approximately 28-40 LPM over the same pressure range. Accordingly, a user can experiment by using a number of moveable membranes 20 until finding one which provides the desired results.

Figure 7:
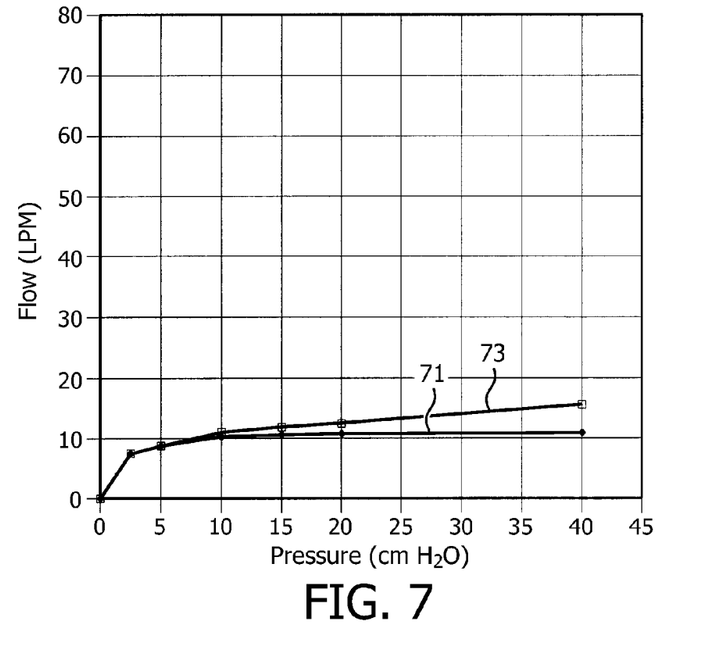
FIG. 7 is a pressure flow curve illustrating the effect of changing the thickness of a moveable membrane within the exhaust assembly.

As another example, FIG. 7 illustrates the flow characteristics for different moveable membranes 20; each with an elastic membrane 21 having a durometer of 10, but each with a different thickness. Generally, an increase in membrane thickness corresponds to a decrease in the deformation of the membrane. A decrease in deformation results in an increase in exhaust flow. The line identified by numeral 71 in FIG. 7, for instance, illustrates that a membrane with a thickness of 0.2 mm (0.008 inches) has a flow plateau level of approximately 10-11 LPM over a pressure range of 10 to 40 cmH$_2$0; whereas the line identified by numeral 73 illustrates a membrane with a thickness of 0.4 mm (0.016 inches) has a flow plateau level of approximately 11-16 LPM over the same pressure range.

Exhaust assembly 1 provides a unique, flow rate control function to ensure an essentially constant exhaust gas flow rate through exhaust vent 31 throughout a range of pressure differentials across the exhaust assembly 1 (i.e., between exhaust gas flow passage 52 and ambient atmosphere). Because the ambient pressure is constant for all practical purposes, a constant exhaust flow rate over a range of pressure differentials means essentially a constant exhaust flow rate over a range of pressures. Such a range of pressures will routinely be observed in exhaust assembly 1, not only because patient breathing effort will generate pressure differences between inhalation and exhalation, but in addition because ventilation systems often are programmed to supply differing levels of pressure in coordination with the patient's breathing. For example, it is known to operate pressure generator 103 in a bi-level mode to deliver a high pressure to the patient during inspiration than during expiration (see for example, U.S. Pat. Nos. 5,148,802 and 5,443,193 the contents of which are hereby incorporated by reference into the present application).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. It is to be understood that the present invention contemplates that, to the extent possible, one or more features of any embodiment can be combined with one or more features of any other embodiment.

What is claimed is:

1. An exhaust assembly adapted for use in a respiratory gas delivery system, comprising:
    an exhaust gas flow passage structured to carry a flow of exhaust gas received in a first end of the exhaust assembly;
    an exhaust vent adapted to communicate the flow of exhaust gas from the exhaust gas flow passage to ambient atmosphere;
    a primary gas flow passage structured to communicate a flow of supply gas from a second end of the exhaust assembly to the first end of the exhaust assembly;
    a moveable member defining at least a portion of the exhaust gas flow passage and at least a portion of the primary gas flow passage; and
    a base portion having a rigid member and a recess, wherein the movable member is received within the recess and the rigid member is received within a slot provided in a bottom of the movable member such that the rigid member and the movable member in conjunction form a partition that divides an interior of the base portion into the exhaust gas flow passage and the primary gas flow passage, wherein the moveable member includes an aperture and a flexible surface, wherein the aperture forms a part of the exhaust gas flow passage, wherein the movable member is operable to isolate the flow of exhaust gas in the exhaust gas flow passage from the flow of supply gas in the primary gas flow passage, wherein the movable member is responsive to a pressure differential between the flow of supply gas in the primary gas flow passage and the flow of exhaust gas in the exhaust gas flow passage, and wherein responsive to ventilation circuit pressures of 10 to 40 cmH$_2$O within the primary gas flow passage: (i) the exhaust gas flow passage is maintained separate and independent from the primary gas flow passage and shares no common portions with the primary gas flow passage such that any flow of gas within the primary gas flow passage is separated from any flow of gas within the exhaust gas flow passage, and (ii) the exhaust gas flow passage is maintained in an open condition to allow the flow of exhaust gas from the first end of the exhaust assembly to the exhaust vent and out to the ambient atmosphere.

2. The exhaust assembly of claim 1, wherein in response to the pressure differential between the flow of supply gas and the flow of exhaust gas, the moveable member is adapted to regulate a rate at which the flow of exhaust gas is communicated to atmosphere through the exhaust vent.

3. The exhaust assembly of claim 2, wherein the moveable member is adapted to regulate the rate at which the flow of exhaust gas is communicated to atmosphere through the exhaust vent by altering the size of the exhaust gas flow passage.

4. The exhaust assembly of claim 3, wherein the moveable member is adapted to decrease the size of the exhaust gas flow passage in response to an increase in the pressure of the flow of supply gas in the primary gas flow passage relative to the pressure of the flow of exhaust gas in the exhaust gas flow passage.

5. The exhaust assembly of claim 1, wherein the first end of the exhaust assembly is adapted to rotatably couple with a patient interface device.

6. The exhaust assembly of claim 1, wherein the second end of the exhaust assembly is adapted to couple with a flow generating device.

7. The exhaust assembly of claim 1, wherein the exhaust vent is provided in a wall of an exhaust portion that is selectively connectable to the base portion such that the moveable member is retained in between the base portion and the exhaust portion.

8. An elbow assembly for a respiratory mask comprising an elbow, wherein the elbow comprises:
    (a) an inlet adapted to couple with a flow generating device; and
    (b) an outlet adapted to couple with a patient interface device, wherein the elbow further defines:
        (1) a primary gas flow passage adapted to communicate a flow of breathing gas from such flow generator to such patient interface device;
        (2) an exhaust vent;
        (3) an exhaust gas flow passage adapted to communicate a flow of exhaust gas from such patient interface device to the exhaust vent, wherein the exhaust vent is adapted to communicate the flow of exhaust gas from the exhaust gas flow passage to atmosphere; and
        (4) a partition disposed in the elbow and structured to isolate the flow of breathing gas within the primary gas flow passage from the flow of exhaust gas in the exhaust gas flow passage, the partition including a moveable member and a base portion having a rigid member and a recess, wherein the movable member is received within the recess and the rigid member is received within a slot provided in a bottom of the movable member such that the rigid member and the movable member in conjunction form the partition and wherein the partition divides an interior of the base portion into the exhaust gas flow passage and the primary gas flow passage, wherein the moveable member includes an aperture and a flexible surface, wherein the aperture forms a part of the exhaust gas flow passage, wherein the movable member is structured to be responsive to a pressure differential between the flow of breathing gas in the primary gas flow passage and the flow of exhaust gas in the exhaust gas flow passage, wherein responsive to ventilation circuit pressures of 10 to 40 cmH$_2$O within the primary gas flow passage: (i) the exhaust gas flow passage is maintained separate and independent from the primary gas flow passage and shares no common portions with the primary gas flow passage such that any flow of gas within the primary gas flow passage is separated from any flow of gas within the exhaust gas flow passage, and (ii) the exhaust gas flow passage is maintained in an open condition to allow the flow of exhaust gas from outlet to the exhaust vent and out to the atmosphere.

9. The elbow assembly of claim 8, wherein in response to the pressure differential between the flow of breathing gas and the flow of exhaust gas, the moveable member is adapted to regulate a rate at which the flow of exhaust gas is communicated to atmosphere through the exhaust vent.

10. The elbow assembly of claim 9, wherein the moveable member is adapted to regulate the rate at which the flow of exhaust gas is communicated to atmosphere through the exhaust vent by altering the size of the exhaust gas flow passage.

11. The elbow assembly of claim 10, wherein the moveable member is adapted to decrease the size of the exhaust gas flow passage in response to an increase in the pressure of the flow of breathing gas in the primary gas flow passage relative to the pressure of the flow of exhaust gas in the exhaust gas flow passage.

12. The elbow assembly of claim 8, wherein the outlet is adapted to rotatably couple with a patient interface device.

13. The exhaust assembly of claim 1, wherein the moveable member has an at rest position and is structured to move away from the at rest position and into the exhaust gas flow passage and reduce an effective cross-sectional area of the exhaust gas flow passage in response to a pressure within the primary gas flow passage exceeding a pressure within the exhaust gas flow passage.

14. The elbow assembly of claim 8, wherein the moveable member has an at rest position and is structured to move away from the at rest position and into the exhaust gas flow passage and reduce an effective cross-sectional area of the exhaust gas flow passage in response to a pressure within the primary gas flow passage exceeding a pressure within the exhaust gas flow passage.

15. The elbow assembly of claim 8, wherein the exhaust vent is provided in a wall of an exhaust portion that is selectively connectable to the base portion such that the moveable member is retained in between the base portion and the exhaust portion.

* * * * *